United States Patent
Yoshitake et al.

(10) Patent No.: US 11,571,447 B2
(45) Date of Patent: Feb. 7, 2023

(54) COMPOSITION FOR PREVENTING, AMELIORATING OR TREATING METABOLIC SYNDROME

(71) Applicant: House Wellness Foods Corporation, Itami (JP)

(72) Inventors: Rieko Yoshitake, Hyogo (JP); Yoshitaka Hirose, Hyogo (JP); Shinji Murosaki, Hyogo (JP); Yusuke Tanaka, Hyogo (JP)

(73) Assignee: HOUSE WELLNESS FOODS CORPORATION, Itami (JP)

( * ) Notice: Subject to any disclaimer, the term of this patent is extended or adjusted under 35 U.S.C. 154(b) by 68 days.

(21) Appl. No.: 16/616,000

(22) PCT Filed: May 23, 2018

(86) PCT No.: PCT/JP2018/019866
§ 371 (c)(1),
(2) Date: Nov. 22, 2019

(87) PCT Pub. No.: WO2018/216735
PCT Pub. Date: Nov. 29, 2018

(65) Prior Publication Data
US 2020/0085889 A1  Mar. 19, 2020

(30) Foreign Application Priority Data

May 26, 2017  (JP) .............................. JP2017-105101

(51) Int. Cl.
| | |
|---|---|
| *A61K 35/747* | (2015.01) |
| *A23L 33/135* | (2016.01) |
| *A61P 3/04* | (2006.01) |
| *A61P 3/06* | (2006.01) |
| *A61P 3/10* | (2006.01) |
| *A61K 9/00* | (2006.01) |

(52) U.S. Cl.
CPC .......... *A61K 35/747* (2013.01); *A23L 33/135* (2016.08); *A61K 9/0095* (2013.01); *A61P 3/04* (2018.01); *A61P 3/06* (2018.01); *A61P 3/10* (2018.01)

(58) Field of Classification Search
None
See application file for complete search history.

(56) References Cited

U.S. PATENT DOCUMENTS

| | | |
|---|---|---|
| 2004/0048356 A1 | 3/2004 | Johansson et al. |
| 2009/0324563 A1 | 12/2009 | Murayama et al. |
| 2010/0098728 A1 | 4/2010 | Fujiki et al. |
| 2014/0065114 A1 | 3/2014 | Lin et al. |
| 2014/0193384 A1 | 7/2014 | Lin et al. |
| 2016/0144041 A1 | 5/2016 | Hirose et al. |

FOREIGN PATENT DOCUMENTS

| | | |
|---|---|---|
| JP | H10-114667 A | 5/1998 |
| JP | H10-167972 A | 6/1998 |
| JP | 2004-121073 | 4/2004 |
| JP | 2004520276 A | 7/2004 |
| JP | 201095465 A | 4/2010 |
| JP | 2010114667 A | 5/2010 |
| JP | 2010167972 A | 8/2010 |
| TW | 201100086 A | 1/2011 |
| TW | 201408311 A | 3/2014 |
| TW | 201620533 A | 6/2016 |
| WO | 2004084923 A1 | 10/2004 |
| WO | 2004084922 | 6/2006 |
| WO | 2008018143 A1 | 2/2008 |
| WO | 2014199448 A1 | 12/2014 |

OTHER PUBLICATIONS

Huang et al., "Supplementation of Lactobacillus Plantarum K68 and Fruit-Vegetable Ferment Along with High Fat-Fructose Diet Attenuates Metabolic Syndrome in Rats with Insulin Resistance," Evidence-Based Complementary and Alternative Medicine, vol. 2013, pp. 1-12. 2013.

Sharafedtinov et al., "Hypocaloric Diet Supplemented with Probiotic Cheese Improves Body Mass Index and Blood Pressure Indices of Obese Hypertensive Patients—A Randomized Bouble-Blind Placebo-Controlled Pilot Study," Nutrition Journal, 12:13B, pp. 1-11, 2013.

Takemura et al., "Lactobacillus Plantarum Strain No. 14 Reduces Adipocyte Size in Mice Fed High-Fat Diet," Experimental Biology and Medicne, vol. 235, pp. 849-856, 2010.

Murosaki et al., "Heat-Killed Lactobacillus Plantarum L-137 Suppresses Naturally Fed Antigen-Specific LgE Production by Stimulation of IL-12 Production in Mice," J Allergy Clin Immunol, 102:1, pp. 57-64, 1998.

Murosaki et al., "Antitumor Effect of Heat-Hilled Lactobacillus Plantarum L-137 through Restoration of Impaired Interleukin-12 Production in Tumor-Bearing Mice," Cancer Immunol Immunother 49:157-164, 2000.

Hirose et al., "Daily Intake of Heat Killed Lactobacillus Plantarum L-137 Augments Acquired Immunity in Healthy Adults," The Journal of Nutrition, 136:12, pp. 3069-3073, 2006.

Maeda et al., "Oral Administration of Heat-Killed Lactobacillus Plantarum L-137 Enhances Protection Against Influenza Virus Infection by Stimulation of Type 1 Interferon Production in Mice," International Immunopharmacology, 9:9, pp. 1122-1125, 2009.

Hirose et al., "Lipoteichoic Acids on Lactobacillus Plantarum Cell Surfaces Correlate with Induction of Interleukin-12p40 Production," 54:3, pp. 143-151, 2010.

(Continued)

*Primary Examiner* — Robert A Zeman
(74) *Attorney, Agent, or Firm* — Wenderoth, Lind & Ponack, L.L.P.

(57) ABSTRACT

An object of the present invention is to provide a therapeutic composition for preventing, ameliorating, or treating metabolic syndrome. The present invention provides a composition for preventing, ameliorating, or treating metabolic syndrome, which composition contains *Lactobacillus plantarum* L-137.

11 Claims, 6 Drawing Sheets
Specification includes a Sequence Listing.

(56) References Cited

OTHER PUBLICATIONS

Arimori et al., "Daily Intake of Heat-Killed Lactobacillus Plantarum L-137 Enhances Type I Interferon Production in Healthy Humans and Pigs," 34:6, pp. 937-943, 2012.

Fujiki et al., "Enhanced Immunomodulatory Activity and Stability in Simulated digestive Juices of Lactobacillus Plantarum L-137 by Heat Treatment," 76:5, pp. 918-922, 2012.

Hirose et al., "Oral Intake of Heat-Killed Lactobacillus Plantarum L-137 Decreases the Incidence of Upper Respiratory Tract Infection in Healthy Subjects with High Levels of Psychological Stress," 2:e39, pp. 1-8, 2013.

Hatano et al., "Scavenger Receptor for Lipoteichoic Acid is Involved in the Potent Ability of Lactobacillus Plantarum Strain L-137 to Stimulate Prodution of Interleukin-12p40," 25:2, pp. 321-331, 2015.

Iwasaki et al., "Daily Intake of Heat-Killed Lactobacillus Plantarum L-137 Decreases the Probing Depth in Patients Undergoing Supportive Periodontal Therapy," 14:3, pp. 207-214, 2016.

Uchinaka et al., "Anti-Inflammatory Effects of Heat-Killed Lactobacillus Plantarum L-137 on Cardiac and Adipose Tissue in Rates with Metabolic Syndrome," Scientific Reports, 8:8156, pp. 1-20, 2018.

International Search Report and the Written Opinion from Corresponding International Application No. PCT/JP2018/019866 dated Jul. 3, 2018, 3 pages.

Takayuki et al., "The Effect of Lactobacillus Plantarum OLL2712 to Improve Lipid Metabolism," Annual Meeting of the Japan Society for Bioscience, Biotechnology and Agrochemistry, pp. 1-3, 2012.

International Preliminary Report on Patentability corresponding to PCT Application No. PCT/JP2018/019866 dated Nov. 26, 2019 (10 pages).

Deen, D. (Jun. 15, 2004) "Metabolic Syndrome: Time for Action", American Family Physician, 69:12, 2875-2882.

Tanaka, Y. et al. (Oct. 16, 2019) "Daily intake of heat-killed Lactobacillus plantarum L-137 improves inflammation and lipid metabolism in overweight healthy adults: a randomized-controlled trial", European Journal of Nutrition, https://doi.org/10.1007/s00394-019-0211203.

Different signs in the same age in weeks means significant difference
($p<0.05$, Tukey-Kramer test-) Mean±SD, N=5

Different signs in the same age in weeks means significant difference
($p<0.05$, Tukey-Kramer test-) Mean±SD, N=5

Different signs in the same age in weeks means significant difference
(p<0.05, Tukey-Kramer test-) Mean±SD, N=5

Mean±SD, N=5

COMPOSITION FOR PREVENTING, AMELIORATING OR TREATING METABOLIC SYNDROME

CROSS REFERENCE TO RELATED APPLICATION

The present application is a National Stage Entry of the International Patent Application No. PCT/JP2018/019866 filed May 23, 2018, which also claims the benefit of priority of the Japanese Patent Application No. 2017-105101 filed May 26, 2017. The entire contents of those applications are incorporated herein for all purposes by this reference.

INCORPORATION BY REFERENCE OF SEQUENCE LISTING

The contents of the sequence listing text file named "050195-502001WO_Sequence_Listing_txt", which was created on Jun. 6, 2018 and is 1,683 bytes in size, are incorporated herein by reference in its entirety.

TECHNICAL FIELD

The present invention relates to a composition for preventing, ameliorating, or treating metabolic syndrome. More specifically, the present invention relates to a composition comprising *Lactobacillus plantarum* L-137 for preventing, ameliorating, or treating metabolic syndrome.

BACKGROUND ART

*Lactobacillus plantarum* L-137 is known to have various functions, such as cold prevention (Patent Literature 1 to 6 and Non Patent Literature 1 to 10), but the function of *Lactobacillus plantarum* L-137 for preventing, ameliorating, or treating metabolic syndrome has been neither known nor even suggested.

CITATION LIST

Patent Literature

Patent Literature 1: JP 2010-95465 A
Patent Literature 2: JP 10-167972 A
Patent Literature 3: WO 2014/199448
Patent Literature 4: WO 2008/018143
Patent Literature 5: WO 2004/084923
Patent Literature 6: WO 2004/084922

Non Patent Literature

Non Patent Literature 1: Iwasaki. et al, Oral Health Prev-Dent., 2016; 14(3):207-14.
Non Patent Literature 2: Hatano. et al, Int Immunopharmacol., 2015; April; 25(2):321-31
Non Patent Literature 3: Hirose. et al, J Nutr Sci., 2013 Dec. 6; 2:e39
Non Patent Literature 4: Fujiki. et al, Biosci Biotechnol Biochem., 2012; 76(5):918-22.
Non Patent Literature 5: Arimori. et al, Immunopharmacol Immunotoxicol. 2012 December; 34(6):937-43
Non Patent Literature 6: Hirose. et al, Microbial Immunol. 2010 March; 54(3):143-51.
Non Patent Literature 7: Maeda. et al, Int Immunopharmacol. 2009 August; 9(9):1122-5.
Non Patent Literature 8: Hirose. et al, J Nutr. 2006 December; 136(12):3069-73.
Non Patent Literature 8: Murosaki. et al, Cancer Immunol Immunother. 2000 June; 49(3):157-64.
Non Patent Literature 10: Murosaki. et al, J Allergy Clin Immunol. 1998 July; 102(1):57-64.

SUMMARY OF INVENTION

Technical Problem

An object of the present invention is to provide a therapeutic composition for preventing, ameliorating, or treating metabolic syndrome.

Solution to Problem

The present inventors found that a composition containing *Lactobacillus plantarum* L-137 (Accession Number: FERM BP-08607 of *Lactobacillus plantarum* L-137, deposited on Nov. 30, 1995 with The National Institute of Technology and Evaluation Patent Microorganisms Depositary (NPMD) and converted to a deposit under the Budapest treaty on Jan. 30, 2004) is useful for preventing, ameliorating, or treating metabolic syndrome. The present inventors conducted further examination and completed the present invention.

That is, the present invention relates to the following.
(1) A therapeutic composition for preventing, ameliorating, or treating metabolic syndrome, the composition containing *Lactobacillus plantarum* L-137.
(2) The composition according to the above (1), which is used for one or more selected from the group consisting of obesity suppression, sugar-or-lipid metabolism disorder amelioration, and inflammatory suppression.
(3) The composition according to the above (1) or (2), which is used for suppressing increase in body weight, adipose tissue weight, and/or liver weight caused by high-fat diet intake, etc.
(4) The composition according to any one of the above (1) to (3), which is used for suppressing increase in blood sugar level, blood cholesterol level, blood insulin level, and/or blood leptin level.
(5) The composition according to any one of the above (1) to (4), which is used for suppressing increase in blood AST (aspartate aminotransferase) level and/or blood ALT (alanine aminotransferase) level, and/or increase in inflammatory gene expression in adipose tissue.
(6) The composition according to any one of the above (1) to (5), which is a food or drink.
(7) The composition according to the above (6), wherein the food or drink is a food additive or a supplement.
(8) A method for preventing, ameliorating, or treating metabolic syndrome, the method comprising the step of administering an effective amount of *Lactobacillus plantarum* L-137 to a subject.
(8-2) The method according to the above (8), wherein *Lactobacillus plantarum* L-137 suppresses obesity, ameliorates sugar-or-lipid metabolism disorder, and/or suppresses inflammation.
(8-3) The method according to the above (8) or (8-2), wherein *Lactobacillus plantarum* L-137 suppresses increase in body weight, adipose tissue weight, and/or liver weight caused by high-fat diet intake, etc.
(8-4) The method according to anyone of the above (8) to (8-3), wherein *Lactobacillus plantarum* L-137 suppresses increase in blood sugar level, blood cholesterol level, blood insulin level, and/or blood leptin level.

(8-5) The method according to anyone of the above (8) to (8-4), wherein *Lactobacillus plantarum* L-137 suppresses increase in blood AST (aspartate aminotransferase) level and/or blood ALT (alanine aminotransferase) level, and/or increase in inflammatory gene expression in adipose tissue.
(8-6) The method according to anyone of the above (8) to (8-5), wherein *Lactobacillus plantarum* L-137 is contained in a food or drink.
(8-7) The method according to the above (8-6), wherein the food or drink is a food additive or a supplement.
(9) *Lactobacillus plantarum* L-137 for use in preventing, ameliorating, or treating metabolic syndrome.
(9-2) The *Lactobacillus plantarum* L-137 according to the above (9), which is used for one or more selected from the group consisting of obesity suppression, sugar-or-lipid metabolism disorder amelioration, and inflammatory suppression.
(9-3) The *Lactobacillus plantarum* L-137 according to the above (9) or (9-2), which is used for suppressing increase in body weight, adipose tissue weight, and/or liver weight caused by high-fat diet intake, etc.
(9-4) The *Lactobacillus plantarum* L-137 according to any one of the above (9) to (9-3), which is used for suppressing increase in blood sugar level, blood cholesterol level, blood insulin level, and/or blood leptin level.
(9-5) The *Lactobacillus plantarum* L-137 according to any one of the above (9) to (9-4), which is used for suppressing increase in blood AST (aspartate aminotransferase) level and/or blood ALT (alanine aminotransferase) level, and/or increase in inflammatory gene expression in adipose tissue.
(9-6) The *Lactobacillus plantarum* L-137 according to any one of the above (9) to (9-5), which is contained in a food or drink.
(9-7) The *Lactobacillus plantarum* L-137 according to the above (8-6), wherein the food or drink is a food additive or a supplement.
(10) Use of *Lactobacillus plantarum* L-137 for the production of a therapeutic medicine for preventing, ameliorating, or treating metabolic syndrome.
(10-2) The use according to the above (10), wherein *Lactobacillus plantarum* L-137 is used for one or more selected from the group consisting of obesity suppression, sugar-or-lipid metabolism disorder amelioration, and inflammatory suppression.
(10-3) The use according to the above (10) or (10-2), wherein *Lactobacillus plantarum* L-137 is used for suppressing increase in body weight, adipose tissue weight, and/or liver weight caused by high-fat diet intake, etc.
(10-4) The use according to anyone of the above (10) to (10-3), wherein *Lactobacillus plantarum* L-137 is used for suppressing increase in blood sugar level, blood cholesterol level, blood insulin level, and/or blood leptin level.
(10-5) The method according to any one of the above (10) to (10-4), wherein *Lactobacillus plantarum* L-137 is used for suppressing increase in blood AST (aspartate aminotransferase) level and/or blood ALT (alanine aminotransferase) level, and/or increase in inflammatory gene expression in adipose tissue.
(10-6) The use according to anyone of the above (10) to (10-5), wherein *Lactobacillus plantarum* L-137 is contained in a food or drink.
(10-7) The use according to the above (10-6), wherein the food or drink is a food additive or a supplement.
(11) Use of *Lactobacillus plantarum* L-137 for preventing, ameliorating, or treating metabolic syndrome.
(11-2) The use according to the above (11), wherein *Lactobacillus plantarum* L-137 is used for one or more selected from the group consisting of obesity suppression, sugar-or-lipid metabolism disorder amelioration, and inflammatory suppression.
(11-3) The use according to the above (11) or (11-2), wherein *Lactobacillus plantarum* L-137 is used for suppressing increase in body weight, adipose tissue weight, and/or liver weight caused by high-fat diet intake, etc.
(11-4) The use according to anyone of the above (11) to (11-3), wherein *Lactobacillus plantarum* L-137 is used for suppressing increase in blood sugar level, blood cholesterol level, blood insulin level, and/or blood leptin level.
(11-5) The method according to any one of the above (11) to (11-4), wherein *Lactobacillus plantarum* L-137 is used for suppressing increase in blood AST (aspartate aminotransferase) level and/or blood ALT (alanine aminotransferase) level, and/or increase in inflammatory gene expression in adipose tissue.
(11-6) The use according to anyone of the above (11) to (11-5), wherein *Lactobacillus plantarum* L-137 is contained in a food or drink.
(11-7) The use according to the above (11-6), wherein the food or drink is a food additive or a supplement.

Advantageous Effects of Invention

The composition of the present invention preferably produces one or more effects selected from (1) an effect of preventing or ameliorating metabolic syndrome, (2) an effect of suppressing obesity, (3) an effect of ameliorating sugar-or-lipid metabolism disorder, (4) an effect of suppressing inflammation, preferably systemic or adipose tissue inflammation, (5) an effect of suppressing increase in body weight caused by, for example, high-fat diet intake etc., (6) an effect of suppressing increase in adipose tissue weight, (7) an effect of suppressing increase in the weight of an organ, such as the liver, (8) an effect of suppressing increase in blood cholesterol level, (9) an effect of suppressing increase in blood insulin level, (10) an effect of suppressing increase in blood leptin level, (11) an effect of suppressing increase in blood AST level, (12) an effect of suppressing increase in blood ALT level, (13) an effect of suppressing increase in expression of inflammatory gene (for example, MCP-1, F4/80, TNF-α, etc.) in adipose tissue, (14) an effect of improving lipid metabolism, (15) an effect of promoting basal metabolism, (16) an effect of reducing body weight, (17) an effect of reducing body fat of a person with obesity or a slightly obese person, (18) an effect of reducing visceral fat or subcutaneous fat, (19) an effect leading to effective dieting, (20) an effect that can be used for preventing or treating obesity, or ameliorating symptoms of obesity, and (21) an effect of promoting reduction in body weight, abdominal fat (visceral fat and subcutaneous fat), and/or waist circumference (waist size).

Preferable effects of the present invention include that even a small dose of the active ingredient can produce an effect of the present invention.

BRIEF DESCRIPTION OF DRAWINGS

In FIG. 2, there is a significant difference between the groups of different signs when comparison is made in the same age in weeks. For example, a and b are different signs but others (a and ab, b and ab, etc.) are not different signs. The same applies to the signs for indicating the presence or absence of a significant difference (a, b, and ab) in FIGS. 3 to 5, 8, and 9.

DESCRIPTION OF EMBODIMENTS

Figure 1:
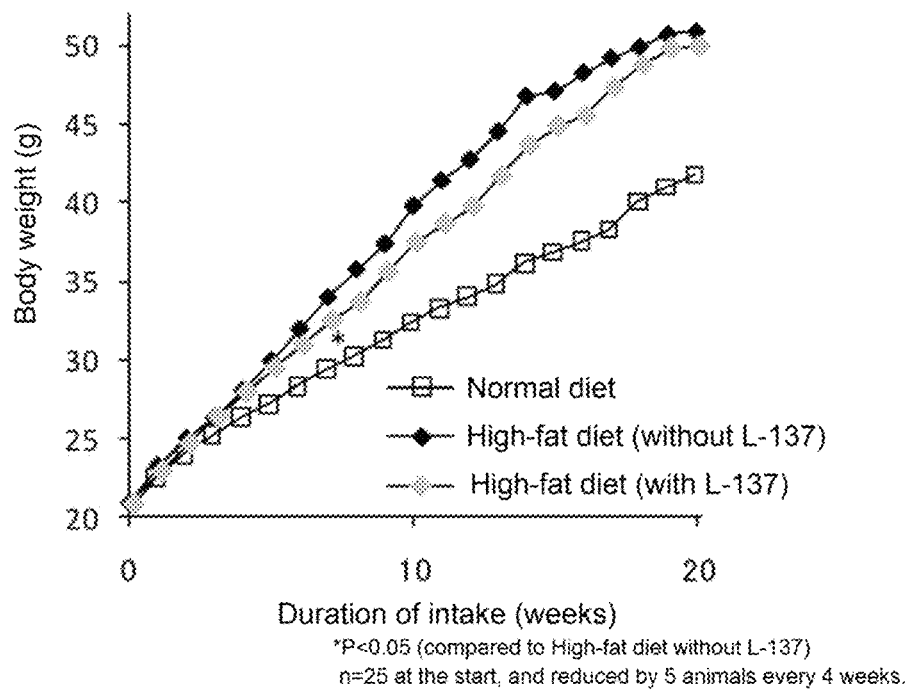
FIG. 1 is a graph showing the changes in body weight during the test period.

The present invention provides a composition for preventing, ameliorating, or treating metabolic syndrome, which composition contains *Lactobacillus plantarum* L-137.

The composition of the present invention contains *Lactobacillus plantarum* L-137. *Lactobacillus plantarum* L-137 is deposited in International Patent Organism Depositary, National Institute of Advanced Industrial Science and Technology (current National Institute of Technology and Evaluation) under Accession Number FERM BP-08607 (transferred from FERM P-15317 deposited on Nov. 30, 1995). Mutants of *Lactobacillus plantarum* L-137 are also in the category of *Lactobacillus plantarum* L-137 as long as the mutants have the characteristics of *Lactobacillus plantarum* L-137.

The composition of the present invention may also contain other components, in addition to *Lactobacillus plantarum* L-137. The components are not particularly limited unless the effects of the present invention are impaired, and for example, any components known in the fields of medicaments, pharmaceuticals, foods, or the like can be used. In one embodiment of the present invention, the components other than *Lactobacillus plantarum* L-137 preferably have a high affinity for the bacterial cells of *Lactobacillus plantarum* L-137 or are capable of binding to *Lactobacillus plantarum* L-137. Examples of such components include a lipid, a sterol, a vegetable oil, a mineral oil, lecithin, etc.

The content of *Lactobacillus plantarum* L-137 in the composition of the present invention is not particularly limited as long as the effects of the present invention are exhibited, and may be, for example, in the range of about 0.001% by mass to 100% by mass.

Method for Obtaining *Lactobacillus plantarum* L-137

The culture of *Lactobacillus plantarum* L-137 may be performed by a publicly known method, a conventional method, or an equivalent method. *Lactobacillus plantarum* L-137 can be obtained by culture on various culture media, such as a natural medium, a synthetic medium, a semisynthetic medium, etc. The culture medium to be used preferably contains a nitrogen source and/or a carbon source. Examples of the nitrogen source include a meat extract, peptone, gluten, casein, a yeast extract, an amino acid, etc., Examples of the carbon source include glucose, xylose, fructose, inositol, maltose, starch syrup, koji extract, starch, bagasse, wheat bran, molasses, glycerol, etc. These may be used alone or in combination of two or more thereof.

In addition to the nitrogen source and/or the carbon source, minerals such as ammonium sulfate, potassium phosphate, magnesium chloride, sodium chloride, iron, manganese and molybdenum; vitamins; etc. may be added alone or in combination of two or more thereof.

In one embodiment of the present invention, the culture temperature of the *Lactobacillus plantarum* L-137 is, for example, usually about 25 to 40° C., and preferably about 27 to 35° C.

In one embodiment of the present invention, the culture duration of the *Lactobacillus plantarum* L-137 is about 12 to 48 hours, optionally with aerated shaking. In one embodiment of the present invention, the culture of *Lactobacillus plantarum* L-137 may be performed with aerated shaking. The pH of the medium is not particularly limited, and usually about pH 3 to 6, preferably about pH 4 to 6.

The bacterial cells of *Lactobacillus plantarum* L-137 may be viable cells or killed cells, but from viewpoints of stability, ease of handling, etc., preferred are killed cells.

After the end of culture, bacterial cells may be collected and then prepared into heat-killed cells. Alternatively, the bacterial cells may be, without prior separation from the culture medium, heat-killed in the culture medium, and then collected. A method for collecting the bacterial cells is, for example, as follows: add distilled water to the culture medium, remove the supernatant by, for example, centrifugation or other means, repeat these as needed, and then collect the bacterial cells by centrifugation, filtration, etc.

The heat-killed cells of *Lactobacillus plantarum* L-137 can be obtained by subjecting collected viable cells or a culture medium containing viable cells to heat treatment for inactivation, followed by drying using an appropriate means, such as spray drying, freeze drying, etc. The heating temperature is usually about 60 to 100° C., preferably about 70 to 90° C. The means for heating may be a publicly known means using a heater. The heating duration is usually about 5 to 40 minutes, preferably about 10 to 30 minutes after the desired temperature is reached.

The killed bacterial cells obtained as above may further be subjected to grinding, crushing, lyophilization, or the like to be prepared into a treated product of killed bacterial cells. In the present invention, the treated product of killed bacterial cells may also be preferably used as killed bacterial cells.

Further, in the present invention, instead of or in addition to the bacterial cells of *Lactobacillus plantarum* L-137, an extract of bacterial cells of *Lactobacillus plantarum* L-137 may be used. The method for obtaining the above extract is not particularly limited, and the extraction may be performed by a publicly known method, a conventional method, or an equivalent method. Specific examples of the method include (i) a method in which viable cells or killed cells of *Lactobacillus plantarum* L-137 are added to a solvent for extraction at a room temperature or an elevated temperature for extraction by immersion and/or with stirring, and (ii) a method in which extraction of viable cells or killed cells of *Lactobacillus plantarum* L-137 is performed in a solvent for extraction under reflux. The extraction temperature and the extraction duration may be appropriately selected depending on extraction conditions including the type of extraction solvent to be used.

The extraction solvent is not particularly limited, and for example, water, an organic solvent, or a mixed solvent thereof at any rate may be used. The organic solvent is not particularly limited, and examples thereof include alcohols that are liquids at room temperature, such as lower alcohols (for example, methanol, ethanol, n-propanol, isopropanol, n-butanol, etc.), polyols (for example, 1,3-butylene glycol, propylene glycol, glycerol, etc.); ethers (for example, diethylether, propyl ether, etc.); esters (for example, ethyl acetate, butyl acetate, etc.); ketones (for example, acetone, ethyl methyl ketone, etc.); hydrocarbons (for example, hexane, xylene, toluene, etc.); chloroform; etc. These may be used alone or in combination of two or more thereof. Of the above organic solvents, alcohols that are liquids at room temperature, for example, lower alcohols having 1 to 4 carbon atoms are preferably used from viewpoints of the ease of handling, environmental impact, etc., and ethanol is more preferably used from a viewpoint of safety regarding residual solvent.

In the present invention, the mixture obtained by the above-described extraction operation, the mixture containing an extraction liquid and residue, may be subjected to filtration or centrifugation as desired to remove solid components as the residue. The extraction liquid may be directly used as it is for the preparation of the composition of the present invention, or dried and powderized by freeze drying, spray drying, or the like before use. The size of bacterial cells of *Lactobacillus plantarum* L-137 may be about 1 to 10 µm.

Usage

The administration route of the composition of the present invention is not particularly limited, and the composition may be orally or parenterally administered to a mammal.

The amount of intake of *Lactobacillus plantarum* L-137 in the case of oral or parenteral administration may be determined depending on the age and body weight of the subject, symptoms, the administration time, the dosage form, the administration method, the combination of medicines, or the like. For example, the amount of intake of *Lactobacillus plantarum* L-137 as killed and dried bacterial cells is preferably set to be about 0.5 to 200 mg, more preferably about 1 to 100 mg, and still more preferably about 2 to 50 mg per adult human (about 60 kg). Alternatively, the amount of intake of *Lactobacillus plantarum* L-137 converted into viable bacterial cells is preferably set to be about $5 \times 10^8$ to $2 \times 10^{11}$ cfu (colony forming unit), more preferably about $1 \times 10^9$ to $1 \times 10^{11}$ cfu per adult human (about 60 kg). The number of times of intake may be once or multiple times per day.

In the case of external application, the amount of applied *Lactobacillus plantarum* L-137 may be appropriately selected depending on the skin area to be treated. Usually, the application amount is preferably about 0.01 to 2.5 mg, more preferably about 0.02 to 1 mg per 10 $cm^2$ per day. The above daily dose may be administered or applied in a single dose or divided multiple doses.

The present invention is excellent also in the point that the effect of the present invention can be achieved even with reduced dose of *Lactobacillus plantarum* L-137.

In oral administration, the composition of the present invention may be a solid pharmaceutical preparation, such as a powder, a granule, a pill, a tablet, and a capsule, or a liquid preparation, such as a syrup. In producing these drugs, carriers or additives suitable for the formulation can be used. Examples of the carrier or additive include an excipient (sodium polyacrylate, calcium polyacrylate, carboxymethylcellulose, lactose, dextrin, cornstarch, crystalline cellulose, saccharose, sodium chloride, glucose, urea, starch, calcium carbonate, kaolin, silicic acid, potassium phosphate, etc.), a lubricant (magnesium stearate, saccharose fatty acid ester, glycerine fatty acid ester, purified talc, polyethylene glycol, etc.), a disintegrator (calcium carboxymethylcellulos, anhydrous dibasic calcium phosphate, sodium carboxymethylcellulose, low substituted hydroxypropylcellulose, dry starch, sodium alginate, agar powder, sodium hydrogencarbonate, calcium carbonate, etc.), a binder (hydroxypropylcellulose, liquid gum arabic, water, ethanol, propanol, simple syrup, dextrose in water, starch in water, gelatin in water, carboxymethylcellulose, methylcellulose, polyvinyl pyrrolidone, etc.), a solubilizer (gum arabic, polysorbate 80, etc.), an absorption enhancer (sodium lauryl sulfate etc.), a buffering agent (phosphate buffer solution, acetate buffer solution, borate buffer solution, carbonate buffer solution, citrate buffer solution, tris buffer solution, etc.), a preservative (methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, disodium edetate, etc.), a thickener (propylene glycol, glycerol, hydroxyethyl cellulose, hydroxypropyl cellulose, polyvinyl alcohol, polyethylene glycol, etc.), a stabilizer (sodium hydrogensulfite, sodium thiosulfate, sodium edetate, sodium citrate, ascorbic acid, dibutyl hydroxytoluene, etc.), and a PH adjustor (hydrochloric acid, sodium hydroxide, phosphoric acid, acetic acid, etc.). As needed, such preparations may be coated with a coating agent (saccharose, gelatin, hydroxypropylcellulose, hydroxypropylmethylcellulose phthalate, or the like), and the coating may consists of 2 or more layers.

The composition of the present invention is not particularly limited, and may be a food or drink, a feed, a food additive, a feed additive, a medicine, a cosmetic product, or the like. Preferred is a food or drink, or the like.

To a food or drink comprising the composition of the present invention, food additives generally used in a food or drink may be added, and examples thereof include a sweetener, a colorant, a preservative, a thickener, an antioxidant, a color improver, a decolorant, an antifungal agent, a gum base, a bittering agent, an enzyme, a brightener, an acidulant, a seasoning, an emulsifier, a fortifier, a processing aid, a flavor, a spice extract, etc. The food or drink includes a food with functional claims, a food for specified health use, a health food, and a food for the sick.

The food or drink suitable for the present invention is not particularly limited. Specific examples thereof include so-called dietary supplements in the form of a tablet, a granule, a powder, or a health drink. Other examples include drinks, such as tea drink, refreshing drink, carbonated drink, nutritional drink, fruit juice, and lactic drink; noodles, such as buckwheat noodle, wheat noodle, Chinese noodle, and instant noodle; sweets and bakery products, such as drop, candy, gum, chocolate, snack, biscuit, jelly, jam, cream, pastry, and bread; fishery or livestock products, such as fish sausage, ham, and sausage; dairy products, such as processed milk and fermented milk; fats, oils, and processed foods thereof, such as vegetable oil, oil for deep frying, margarine, mayonnaise, shortening, whipped cream, and dressing; seasonings, such as sauce and dipping sauce; retort pouch foods, such as curry, stew, rice-bowl cuisine, porridge, and rice soup; frozen desserts, such as ice cream, sherbet, and shaved ice; etc.

In the cases where the composition of the present invention is prepared into the form of a food or drink, one or more selected from the following effects of the composition of the present invention: (1) preventing or ameliorating metabolic syndrome, (2) suppressing obesity, (3) ameliorating sugar- or-lipid metabolism disorder, (4) suppressing inflammation, preferably systemic or adipose tissue inflammation, (5)

suppressing an increase in body weight caused by, for example, high-fat diet intake etc., (6) suppressing an increase in adipose tissue weight, (7) suppressing increase in the weight of an organ, such as the liver, (8) suppressing increase in blood cholesterol level, (9) suppressing increase in blood insulin level, (10) suppressing increase in blood leptin level, (11) suppressing increase in blood AST level, (12) suppressing increase in blood ALT level, (13) suppressing increase in expression of inflammatory gene (for example, MCP-1 (monocyte chemotactic protein 1), F4/80 (anti-EGF-like module-containing mucin-like receptor 1), TNF-α (tumor necrosis factor-alpha), etc.) in adipose tissue, (14) improving lipid metabolism, (15) promoting basal metabolism, (16) reducing body weight, (17) reducing body fat of a person with obesity or a slightly obese person, (18) reducing visceral fat or subcutaneous fat, (19) leading to effective dieting, (20) being used for preventing or treating obesity, or ameliorating symptoms of obesity, (21) promoting reduction in body weight, abdominal fat (visceral fat and subcutaneous fat), and/or waist circumference (waist size) and (22) being suitably used by a person concerned about body fat, abdominal circumference (waist size), body weight, BMI, and/or abdominal fat (visceral fat and subcutaneous fat may be indicated on the food or drink, the attached description, the package box, or the like.

A high-fat food is, for example, a food composition of which the lipid to energy ratio is 30% or more (preferably 30 to 60%), or a food composition having fat content of 10 g or more (preferably 20 to 100 g, more preferably 30 to 100 g, more preferably 40 to 100 g, more preferably 50 to 100 g, more preferably 60 to 100 g) relative to 100 g of the food composition.

The lipid to energy ratio can be calculated by the following formula.

Lipid to energy ratio (%)={fat content (g)×9 kcal/ total energy(kcal)}×100

Examples of the high-fat food include meats, such as beef flank, beef (sirloin), pork belly, bacon, salami, sausage, foie gras, and frankfurt; fish and seafood, such as liver of sea toad, fatty tuna, sardine (in oil), Pacific saury, tuna, grilled eel, sliced raw young yellowtail, yellowtail, sablefish, salted salmon roe in ovarian membrane, and salmon roe; cereal products, such as croissant, danish pastry, and instant noodle; egg and dairy products, such as egg yolk, whipped cream, cream cheese, process cheese, butter, and ice cream; bean products, such as deep-fried tofu and soybean flour; nuts, such as macadamia nut, pinenut, walnut, sesame, almond, peanut, and cashew nut; vegetables and tuberous crops, such as avocado and fried potato; beverages, such as coconut milk; confectionary, such as potato chips, chocolate, biscuit, and popcorn; and seasonings, such as mayonnaise, French dressing, olive oil, chili oil, and peanut butter; and foods having these as ingredients.

Examples of the feed comprising the composition of the present invention include a feed for livestock such as a cow, a horse, and a pig; a feed for poultry such as a chicken; and a feed for pet animals, such as a dog and a cat. The feed of the present invention can be processed and produced with use of an ordinary production method except for addition of the composition of the present invention to the feed.

The composition of the present invention may be contained in medicines. The medicines can be produced by blending *Lactobacillus plantarum* L-137 with publicly known additives for medicines etc.

The composition of the present invention may also be contained in cosmetics. Examples of the cosmetics include cleansing preparations such as body wash, hand wash and face wash; skin-care preparations such as lotion, milky lotion and cream; make-up preparations such as foundation, under makeup base and face powder; etc.

The composition of the present invention preferably produces one or more effects selected from (1) an effect of preventing or ameliorating metabolic syndrome, (2) an effect of suppressing obesity, (3) an effect of ameliorating sugar-or-lipid metabolism disorder, (4) an effect of suppressing inflammation, preferably systemic or adipose tissue inflammation, (5) an effect of suppressing an increase in body weight caused by, for example, high-fat diet intake etc; (6) an effect of suppressing an increase in adipose tissue weight, (7) an effect of suppressing increase in the weight of an organ, such as the liver, (8) an effect of suppressing increase in blood cholesterol level, (9) an effect of suppressing increase in blood insulin level, (10) an effect of suppressing increase in blood leptin level, (11) an effect of suppressing increase in blood AST level, (12) an effect of suppressing increase in blood ALT level, (13) an effect of suppressing increase in expression of inflammatory gene (for example, MCP-1, F4/80, TNF-α, etc.) in adipose tissue, (14) an effect of improving lipid metabolism, (15) an effect of promoting basal metabolism, (16) an effect of reducing body weight, (17) an effect of reducing body fat of a person with obesity or a slightly obese person, (18) an effect of reducing visceral fat or subcutaneous fat, (19) an effect leading to effective dieting, (20) an effect that can be used for preventing or treating obesity, or ameliorating symptoms of obesity, and (21) an effect of promoting reduction in body weight, abdominal fat (visceral fat and subcutaneous fat), and/or waist circumference (waist size).

The effect of suppressing obesity means, for example, suppressing increase in body weight, adipose tissue weight, and/or weight of an organ such as the liver caused by high-fat diet intake, etc. Since the increase in weight of an organ such as the liver caused by high-fat diet intake, etc. is accompanied by fatty liver, suppressing the increase holds promise for ameliorating fatty liver as well.

The effect of ameliorating sugar metabolism disorder means, for example, suppressing increase in blood sugar level, blood insulin level, etc.

The effect of ameliorating lipid metabolism disorder means, for example, suppressing increase in blood cholesterol level, blood leptin level, etc.

The effect of suppressing inflammation means, for example, increase in blood AST level and/or blood ALT level, and/or increase in expression of inflammatory gene (MCP-1, F4/80, TNF-α, etc.) in adipose tissue.

The effect of suppressing inflammation may be an effect on systemic inflammation or on adipose tissue inflammation.

Examples

Hereinafter, the present invention will be illustrated in more detail by Examples and Test Examples, but the present invention is not limited thereto.

Experimental Method

C57BL/6J mice (male, 6 weeks old) were purchased from Charles River Japan, and were fed with CE-2 for 7 days for acclimation.

Then, the mice were divided into groups so that each group consists of 25 mice and has almost the same average body weight. Each group was fed with a test diet, namely, normal diet (AIN-93G; see Table 1), 60% high-fat diet (cal %;

calorie %) (see Table 2), or 60% high-fat diet (cal %; calorie %) (see Table 2) containing 0.002% by mass of heat-killed bacterial cells of *Lactobacillus plantarum* L-137 (HK L-137) for 20 weeks.

TABLE 1

Composition of normal diet (AIN-93G Oriental Yeast)

| Weight (g) | |
|---|---|
| Cornstarch | 397.486 |
| Milk casein | 200 |
| Gelatinized cornstarch | 132 |
| Granulated sugar | 100 |
| Purified soybean oil | 70 |
| Cellulose powder | 50 |
| Mineral mix | 35 |
| Vitamin mix | 10 |
| L-cystine | 3 |
| Choline bitartrate | 2.5 |
| Tertiary butylhydroquinone | 0.014 |
| Total | 1000 |

TABLE 2

Composition of high-fat diet (HFD-60 Oriental Yeast)

| Weight (g) | Without L-137 | With L-137 |
|---|---|---|
| Soybean oil | 20 | 20 |
| Lard | 330 | 330 |
| Milk casein | 256 | 256 |
| Maltodextrin | 60 | 60 |
| Gelatinized cornstarch | 160 | 160 |
| LP20 | — | 100 mg |
| Calcium carbonate | 1.8 | 1.8 |
| Choline bitartrate | 2.5 | 2.5 |
| L-cystine | 3.6 | 3.6 |
| AIN-93G vitamin mix | 10 | 10 |
| AIN-93G mineral mix | 35 | 35 |
| Sucrose | 55 | 55 |
| Cellulose powder | 66.1 | 66.1 |
| Total | 1000 | 1000 |

*LP20 is a dextrin powder containing 20%(w/w) of HKL-137.

During the test period, each mouse was individually accommodated in a cage under environment with a light-dark cycle of 12 hours at a room temperature of 23±3° C. and was fed with the diet and water ad libitum, and the body weight was measured every week.

Every 4 weeks of intake, 5 animals representative of each group (the average body weight and the standard deviation (SD) are almost the same as those of the whole group) were taken from each group. Each mouse was ether-anesthetized not in fasting, and blood was collected from vena cava using a heparin-treated syringe. In addition, peritesticular fat tissue and the liver were collected and weighed.

The collected blood was centrifuged (2000×g, 20 minutes) to obtain plasma, and the plasma was subjected to measurements of blood sugar level, blood total cholesterol level, blood AST level, blood ALT level, blood insulin level, and blood leptin level using commercially available kits (Glucose CII-Test Wako, Cholesterol E-Test Wako, and Transaminase CII-Test Wako by Wako Pure Chemical, Mouse Insulin ELISA Kit and Mouse/Rat Leptin ELISA Kit by Morinaga Institute of Biological Science).

The peritesticular fat tissue was immersed in RNAlater (Thermo Fisher Scientific) and was stored at −80° C. After thawed, RNA extraction (Rneasy Lipid Tissue Mini Kit, QIAGEN) was performed. The extracted RNA was subjected to measurement of inflammatory genes (monocyte chemotactic protein 1 (MCP-1), anti-EGF-like module-containing mucin-like receptor 1 (F4/80), and tumor necrosis factor-alpha (TNF-alpha)) and an internal control gene (beta-actin) using the following enzymes and the instrument (One Step SYBR PrimeScript RT-PCR Kit II by Takara, and Thermal Cycler Dice TP800 by Takara) (for primers, see Table 3). Then, the expression levels of the inflammatory genes corrected with the internal control gene were calculated.

TABLE 3

| Gene Name | Length to be amplified (bp) | Direction | Sequence 5'-3' |
|---|---|---|---|
| MCP-1 | 103 | Forward | GACCCCAAGAAGGAATGGGT |
| | | Reverse | ACCTTAGGGCAGATGCAGTT |
| F4/80 | 110 | Forward | TGACTCACCTTGTGGTCCTAA |
| | | Reverse | CTTCCCAGAATCCAGTCTTTCC |
| TNF alpha | 147 | Forward | CCTGTAGCCCACGTCGTAG |
| | | Reverse | GGGAGTAGACAAGGTACAACCC |
| Beta-actin | 154 | Forward | GGCTGTATTCCCCTCCATCG |
| | | Reverse | CCAGTTGGTAACAATGCCATGT |

Experimental Results

1. Effect of Suppressing Obesity

Figure 2:
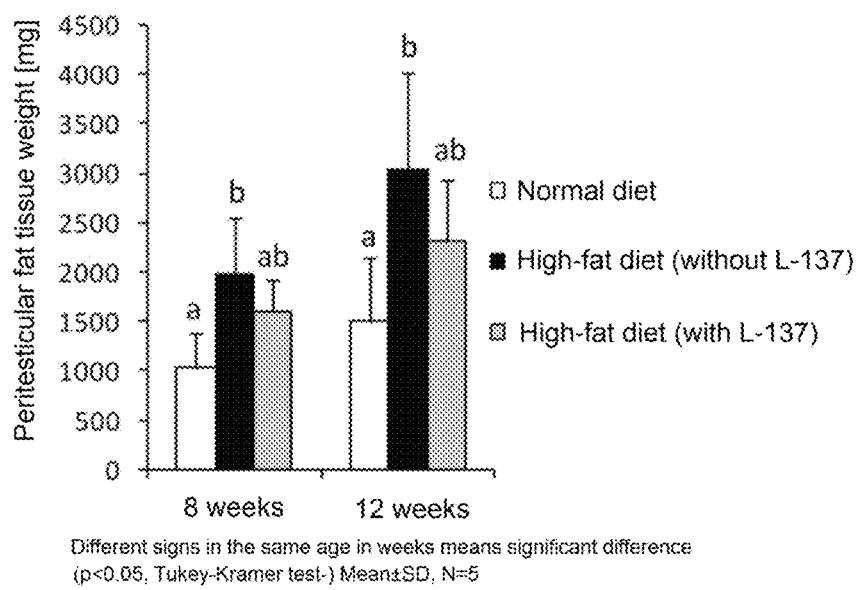
FIG. 2 is a graph showing the weights of peritesticular fat tissue after 8-week and 12-week feed intake.
Figure 3:
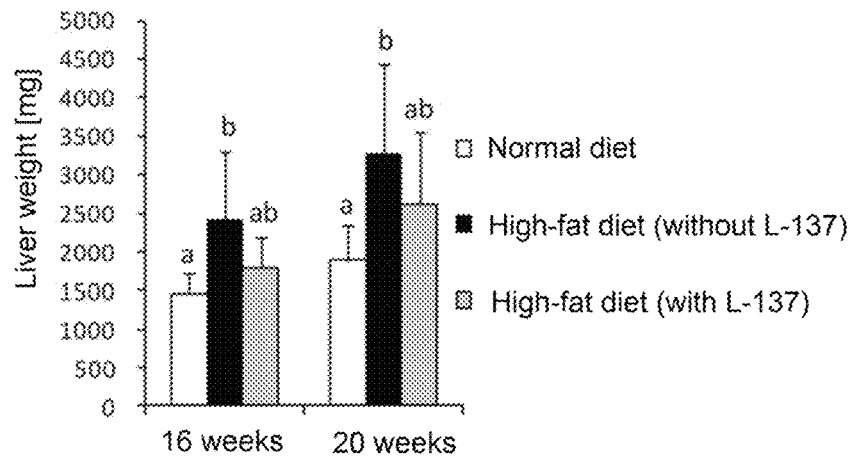
FIG. 3 is a graph showing the liver weights after 16-week and 20-week feed intake.

The changes in body weight during the test period are shown in Table 4 and FIG. 1, the weights of peritesticular fat tissue after 8-week and 12-week feed intake are shown in Table 5 and FIG. 2, and the liver weights after 16-week and 20-week feed intake are shown in Table 6 and FIG. 3.

The results confirmed that *Lactobacillus plantarum* L-137 suppresses increase in body weight, adipose tissue weight, and liver weight caused by high-fat diet intake.

TABLE 4

| Body weight (g) | Starting day of rearing | 8-week intake |
|---|---|---|
| Normal diet | 20.87 | 30.21 |
| High-fat diet (without L-137) | 20.90 | 35.76 |
| High-fat diet (with L-137) | 20.88 | 33.70* |

TABLE 5

| Peritesticular fat tissue weight (mg) | 8-week intake | 12-week intake |
|---|---|---|
| Normal diet | 1024 | 1500 |
| High-fat diet (without L-137) | 1984 | 3031 |
| High-fat diet (with L-137) | 1600 | 2313 |

TABLE 6

| Liver weight (mg) | 16-week intake | 20-week intake |
|---|---|---|
| Normal diet | 1458 | 1894 |
| High-fat diet (without L-137) | 2399 | 3266 |
| High-fat diet (with L-137) | 1798 | 2620 |

2. Effect of Ameliorating Sugar-or-Lipid Metabolism Disorder

Figure 4:
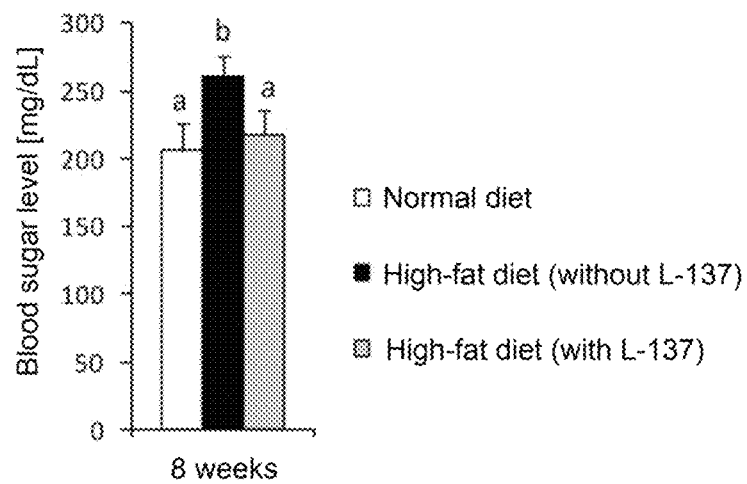
FIG. 4 is a graph showing the blood sugar levels after 8-week feed intake.
Figure 5:
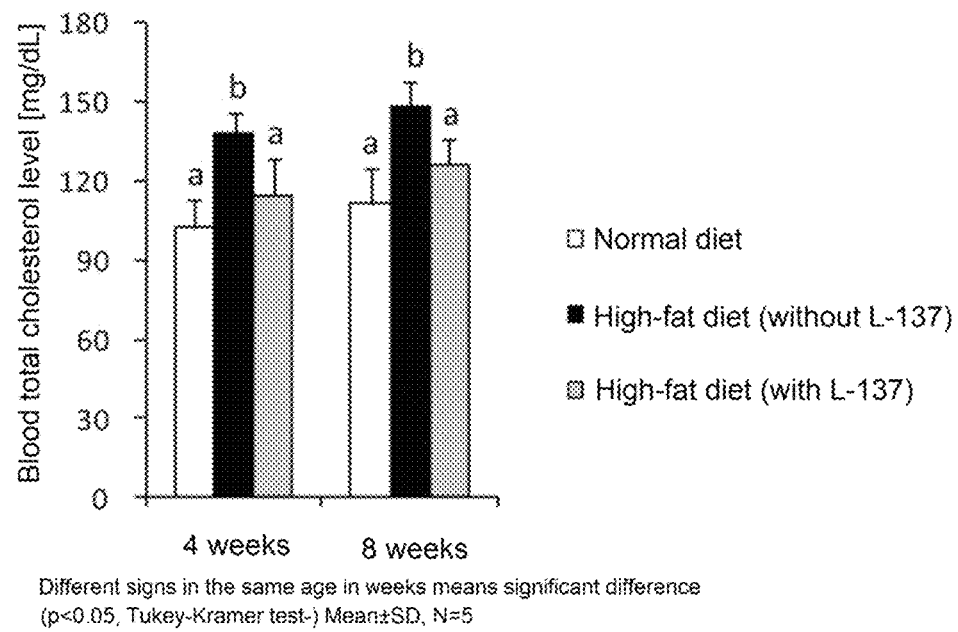
FIG. 5 is a graph showing the total cholesterol levels after 4-week and 8-week feed intake.
Figure 6:
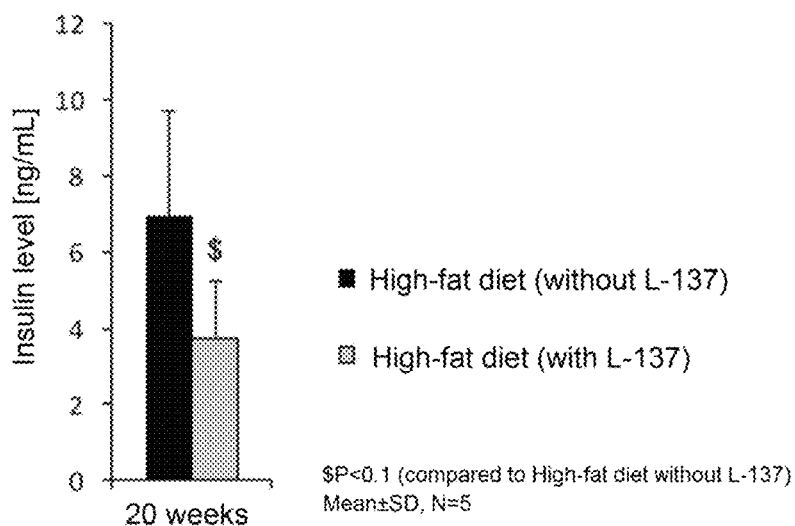
FIG. 6 is a graph showing the blood insulin levels after 20-week feed intake.
Figure 7:
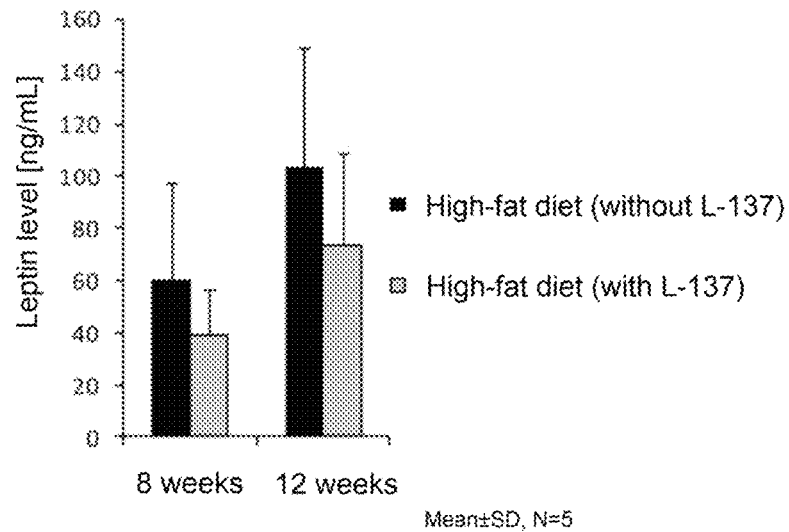
FIG. 7 is a graph showing the blood leptin levels after 8-week and 12-week feed intake.

The blood sugar levels after 8-week feed intake are shown in Table 7 and FIG. 4, the total cholesterol levels after 4-week and 8-week feed intake are shown in Table 8 and FIG. 5, the blood insulin levels after 20-week feed intake are shown in Table 9 and FIG. 6, and the blood leptin levels after 8-week and 12-week feed intake are shown in Table 10 and FIG. 7.

The results confirmed that *Lactobacillus plantarum* L-137 suppresses increase in blood sugar level, blood total cholesterol level, and blood insulin level caused by high-fat diet intake. The results also confirmed that *Lactobacillus plantarum* L-137 has a tendency to suppress increase in the leptin level caused by high-fat diet intake.

TABLE 7

| Blood sugar level (mg/dL) | 8-week intake |
|---|---|
| Normal diet | 206 |
| High-fat diet (without L-137) | 262 |
| High-fat diet (with L-137) | 218 |

TABLE 8

| Blood total cholesterol level (mg/dL) | 4-week intake | 8-week intake |
|---|---|---|
| Normal diet | 112 | 134 |
| High-fat diet (without L-137) | 139 | 148 |
| High-fat diet (with L-137) | 115 | 127 |

TABLE 9

| Blood insulin level (ng/mL) | 20-week intake |
|---|---|
| High-fat diet (without L-137) | 6.93 |
| High-fat diet (with L-137) | 3.77 |

TABLE 10

| Blood leptin level (ng/mL) | 8-week intake | 12-week intake |
|---|---|---|
| High-fat diet (without L-137) | 60.2 | 103.5 |
| High-fat diet (with L-137) | 39.2 | 73.6 |

3. Effect of Suppressing Inflammation

Figure 8:
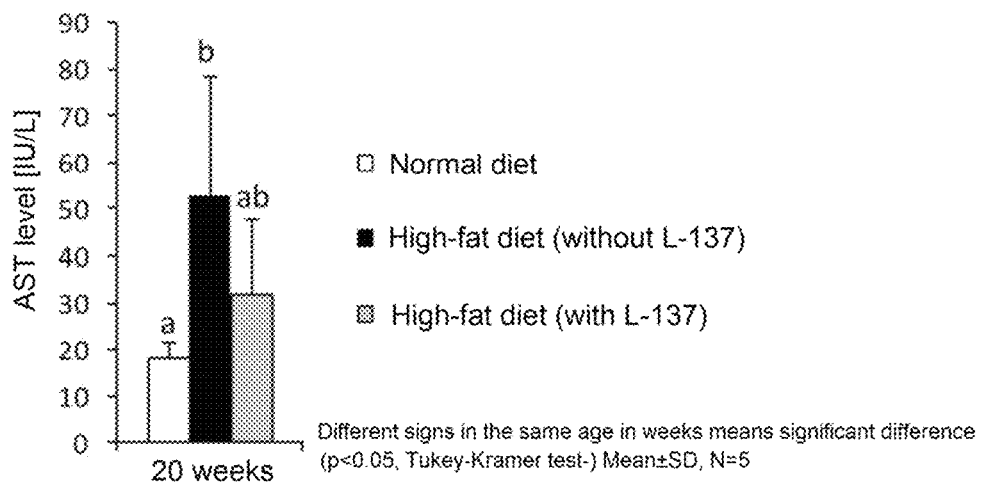
FIG. 8 is a graph showing the blood AST levels after 20-week feed intake.
Figure 9:
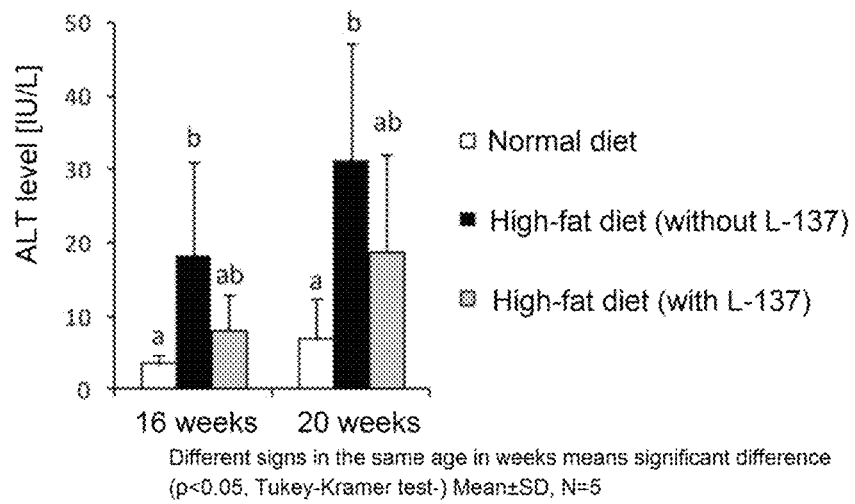
FIG. 9 is a graph showing the blood AST levels after 16-week and 20-week feed intake.
Figure 10:
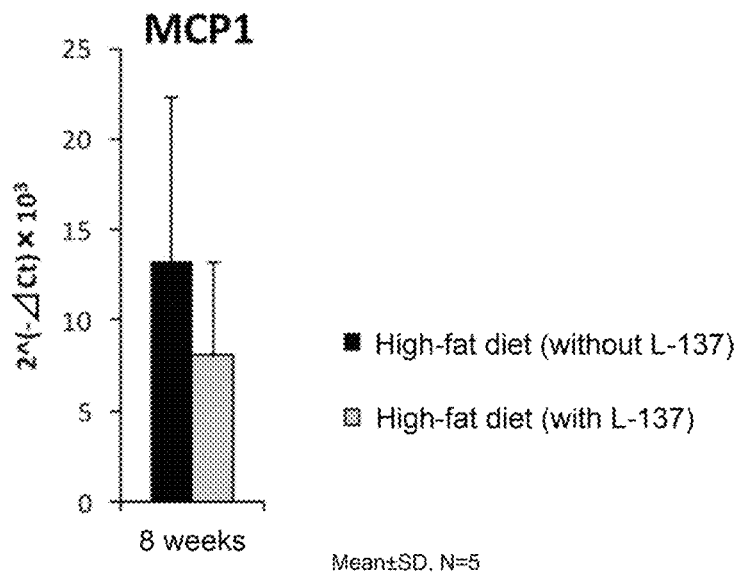
FIG. 10 is a graph showing the relative expression levels of the MCP1 gene after 8-week feed intake.
Figure 11:
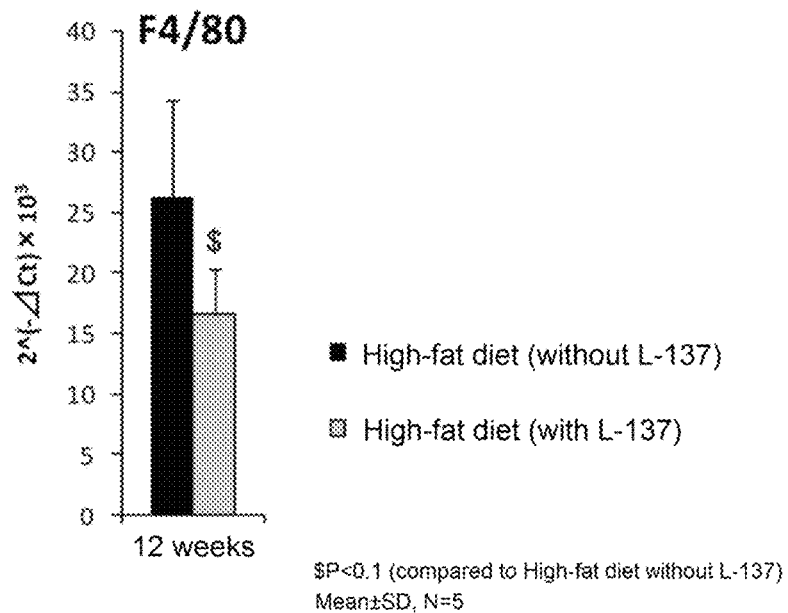
FIG. 11 is a graph showing the relative expression levels of the F4/80 gene after 12-week feed intake.
Figure 12:
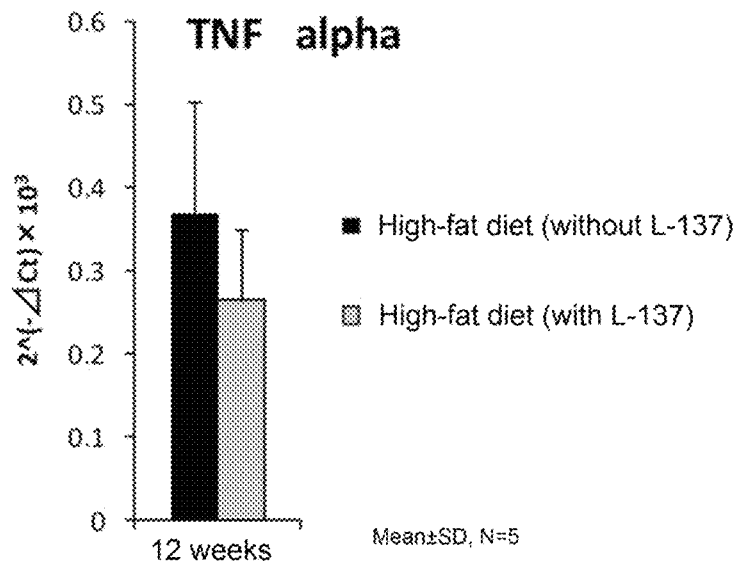
FIG. 12 is a graph showing the relative expression levels of the TNF-α gene after 12-week feed intake.

The blood AST levels after 20-week feed intake are shown in Table 11 and FIG. 8, the blood AST levels after 16-week and 20-week feed intake are shown in Table 12 and FIG. 9, the relative expression levels of the MCP1 gene after 8-week feed intake are shown in Table 13 and FIG. 10, the relative expression levels of the F4/80 gene after 12-week feed intake are shown in Table 13 and FIG. 11, and the relative expression levels of the TNF-α gene after 12-week feed intake are shown in Table 13 and FIG. 12.

The results confirmed that *Lactobacillus plantarum* L-137 suppresses increase in blood AST level, blood ALT level, and expression levels of inflammatory genes caused by high-fat diet intake.

TABLE 11

| Blood AST level (IU/L) | 20-week intake |
|---|---|
| Normal diet | 18.2 |
| High-fat diet (without L-137) | 52.8 |
| High-fat diet (with L-137) | 31.9 |

TABLE 12

| Blood ALT level (IU/L) | 16-week intake | 20-week intake |
|---|---|---|
| Normal diet | 3.42 | 134 |
| High-fat diet (without L-137) | 139 | 148 |
| High-fat diet (with L-137) | 115 | 127 |

TABLE 13

| MCP1 ($2^{(-\Delta Ct)} \times 10^3$) | 8-week intake |
|---|---|
| High-fat diet (without L-137) | 13.2 |
| High-fat diet (with L-137) | 8.1 |
| F4/80 ($2^{(-\Delta Ct)} \times 10^3$) | 12-week intake |
| High-fat diet (without L-137) | 26.1 |
| High-fat diet (with L-137) | 16.5 |
| TNF alpha ($2^{(-\Delta Ct)} \times 10^3$) | 12-week intake |
| High-fat diet (without L-137) | 0.368 |
| High-fat diet (with L-137) | 0.264 |

The results show that *Lactobacillus plantarum* L-137 is useful for preventing, ameliorating, or treating metabolic syndrome.

INDUSTRIAL APPLICABILITY

The composition of the present invention is useful as a food or drink, a medicine, or a feed for the purposes of dieting; the prevention or amelioration of obesity; and also the prevention, amelioration, or treatment of metabolic syndrome leading to diabetes, hypertriglyceridemia, hypercholesterolemia, arteriosclerosis, etc.

The invention claimed is:

1. A method for ameliorating a metabolic symptom, the method comprising the step of orally or parenterally administering an effective amount of *Lactobacillus plantarum* L-137 (Accession Number: FERM BP-08607) to a subject, and wherein the metabolic symptom comprises one of the following:
- an increase in body weight, an increase adipose tissue weight, and/or an increase in liver weight;
- an increase in blood sugar level;
- an increase in blood cholesterol level, an increase in blood insulin level, and/or an increase in blood leptin level; or
- an increase in blood aspartate aminotransferase (AST) level and/or an increase in blood alanine aminotransferase (ALT) level, and/or an increase in inflammatory gene expression in adipose tissue.

2. The method according to claim 1, wherein the *Lactobacillus plantarum* L-137 further ameliorates obesity, sugar- or-lipid metabolism disorder, and/or inflammation.

3. The method according to claim 1, wherein the *Lactobacillus plantarum* L-137 further ameliorates an increase in blood sugar level, blood cholesterol level, blood insulin level, and/or blood leptin level.

4. The method according to claim 1, wherein the *Lactobacillus plantarum* L-137 further ameliorate an increase in blood AST level and/or blood ALT level, and/or increase in inflammatory gene expression in adipose tissue.

5. The method according to claim 1, wherein the *Lactobacillus plantarum* L-137 is contained in a food or drink.

6. The method according to claim 5, wherein the food or drink is a food additive or a supplement.

7. The method according to claim 1, wherein the subject is a mammal.

8. The method according to claim 1, wherein the *Lactobacillus plantarum* L-137 is orally administered.

9. The method according to claim 1, wherein the effective amount of *Lactobacillus plantarum* L-137 is $5\times10^8$ to $2\times10^{11}$ cfu (colony forming unit)/day in case of an adult human.

10. The method according to claim 9, wherein the effective amount of *Lactobacillus plantarum* L-137 is $1\times10^9$ to $1\times10^{11}$ cfu (colony forming unit)/day in case of an adult human.

11. The method according to claim 1, wherein the inflammatory gene is one or more selected from the group consisting of MCP-1 (monocyte chemotactic protein 1), F4/80 (anti-EGF-like module-containing mucin-like receptor 1) and TNF-α (tumor necrosis factor-alpha).

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gaccccaaga aggaatgggt                                       20

<210> SEQ ID NO 2

```
<211> LENGTH: 20
<212> TYPE: DNA
<213> ORGANISM: Artificial Sequence
<220> FEATURE:
<223> OTHER INFORMATION: primer

<400> SEQUENCE: 2
accttagggc agatgcagtt                                               20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
tgactcacct tgtggtccta a                                             21

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
cttcccagaa tccagtcttt cc                                            22

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
cctgtagccc acgtcgtag                                                19

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
gggagtagac aaggtacaac cc                                            22

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggctgtattc ccctccatcg                                               20

<210> SEQ ID NO 8
<211> LENGTH: 22
<212> TYPE: DNA
```

```
<213> ORGANISM: Artificial Sequence
<220> FEATURE:
<223> OTHER INFORMATION: primer

<400> SEQUENCE: 8
ccagttggta acaatgccat gt                                              22
```